United States Patent
Kim et al.

(10) Patent No.: US 10,952,633 B2
(45) Date of Patent: Mar. 23, 2021

(54) METHOD AND APPARATUS FOR MEASURING BIOIMPEDANCE

(71) Applicant: Samsung Electronics Co., Ltd., Suwon-si (KR)

(72) Inventors: JongPal Kim, Seoul (KR); TakHyung Lee, Suwon-si (KR); Hyoung Ho Ko, Daejeon (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 337 days.

(21) Appl. No.: 16/012,809

(22) Filed: Jun. 20, 2018

(65) Prior Publication Data
US 2018/0296120 A1    Oct. 18, 2018

Related U.S. Application Data
(63) Continuation of application No. 14/562,193, filed on Dec. 5, 2014, now Pat. No. 10,022,064.

(30) Foreign Application Priority Data
Jul. 17, 2014   (KR) .......................... 10-2014-0090620

(51) Int. Cl.
*A61B 5/053*    (2021.01)
*A61B 5/00*     (2006.01)

(52) U.S. Cl.
CPC ............ *A61B 5/053* (2013.01); *A61B 5/7225* (2013.01); *A61B 5/6804* (2013.01)

(58) Field of Classification Search
CPC ........................................... A61B 5/053–0538

USPC .................................................. 600/547, 548
See application file for complete search history.

(56) References Cited

U.S. PATENT DOCUMENTS

| | | | |
|---|---|---|---|
| 5,749,369 A | 5/1998 | Rabinovich et al. | |
| 7,203,536 B2 | 4/2007 | Masuo | |
| 7,711,414 B2 * | 5/2010 | Shin ..................... | A61B 5/0428 600/509 |
| 8,487,686 B2 | 7/2013 | Ironstone et al. | |
| 8,862,210 B2 | 10/2014 | Yazicioglu et al. | |
| 2003/0216661 A1 | 11/2003 | Davies | |

(Continued)

FOREIGN PATENT DOCUMENTS

| | | |
|---|---|---|
| EP | 2 298 164 A2 | 3/2011 |
| JP | 2001-70273 A | 3/2001 |

(Continued)

OTHER PUBLICATIONS

Extended European Search Report dated Nov. 26, 2015, in corresponding European Patent Application No. 15152048.3, (9 pages in English).

(Continued)

*Primary Examiner* — David J. McCrosky
(74) *Attorney, Agent, or Firm* — NSIP Law

(57) ABSTRACT

A method and an apparatus for measuring a bioimpedance are disclosed. The apparatus includes a first electrical signal generator configured to generate a first electrical signal to measure a bioimpedance of an object. The apparatus also includes a compensation signal generator configured to generate a compensation signal to compensate a biosignal measured based on the first electrical signal, and an amplifier configured to amplify the compensated biosignal.

15 Claims, 15 Drawing Sheets

(56) References Cited

U.S. PATENT DOCUMENTS

| | | |
|---|---|---|
| 2005/0192488 A1 | 9/2005 | Bryenton et al. |
| 2005/0203437 A1 | 9/2005 | Shambroom et al. |
| 2005/0259371 A1 | 11/2005 | Henze et al. |
| 2006/0015033 A1 | 1/2006 | Blakley et al. |
| 2006/0129333 A1 | 6/2006 | Ashida et al. |
| 2010/0290675 A1 | 11/2010 | Wexler et al. |
| 2011/0251817 A1 | 10/2011 | Burns et al. |
| 2013/0102920 A1 | 4/2013 | Fan et al. |
| 2013/0338661 A1 | 12/2013 | Behnke, II |

FOREIGN PATENT DOCUMENTS

| | | |
|---|---|---|
| JP | 2001-340313 A | 12/2001 |
| JP | 2009-136667 A | 6/2009 |
| JP | 4525995 B2 | 8/2010 |
| JP | 2011-78443 A | 4/2011 |
| JP | 2012-210355 A | 11/2012 |
| JP | 2013-128716 A | 7/2013 |
| JP | 2013-150790 A | 8/2013 |
| JP | 2013-183767 A | 9/2013 |
| KR | 2000-0075585 A | 12/2000 |
| KR | 10-0864415 B1 | 10/2008 |
| KR | 10-0868071 B1 | 11/2008 |
| KR | 10-2009-0104908 A | 10/2009 |
| KR | 10-2010-0061824 A | 6/2010 |
| KR | 10-1030507 A | 4/2011 |
| KR | 10-2011-0108186 A | 10/2011 |
| KR | 10-1101118 B1 | 1/2012 |
| KR | 10-1345640 B1 | 10/2013 |
| KR | 10-1359054 B1 | 12/2013 |
| KR | 10-2014-0007994 A | 1/2014 |

OTHER PUBLICATIONS

Annus, Paul et al., "Design of a Bioimpedance Measurement System Using Direct Carrier Compensation", *Proceedings of the 2005 European Conference on Circuit Theory and Design,* vol. 3, 2005 (4 pages in English).

* cited by examiner

METHOD AND APPARATUS FOR MEASURING BIOIMPEDANCE

CROSS-REFERENCE TO RELATED APPLICATION

This application is a continuation of U.S. application Ser. No. 14/562,193 filed on Dec. 5, 2014 which claims the benefit under 35 USC § 119(a) of Korean Patent Application No. 10-2014-0090620, filed on Jul. 17, 2014, in the Korean Intellectual Property Office, the entire disclosure of which is incorporated herein by reference for all purposes.

BACKGROUND

1. Field

The following description relates to a method and an apparatus to measure bioimpedance.

2. Description of Related Art

Skin, blood, muscles, tissues, joints, and other portions or organs of a body produce an impedance with a value including a resistance component and a capacitor component in response to current flowing through the body. The impedance value refers to a bioimpedance. Based on the bioimpedance, body fat or body fluid components may be estimated. The bioimpedance is obtained by applying a low-frequency current signal to a body of a user and measuring a voltage signal between measurement electrodes.

A bioelectrode used to measure the bioimpedance includes a wet electrode and a dry electrode. The wet electrode uses an electrolyte solution for surface treatment to reduce an interface impedance of a surface on which the electrode and skin of the user are contacted. Conversely, the dry electrode does not use an electrolyte to measure a biosignal, for example, the bioimpedance. As a result, the dry electrode has a greater interface impedance than the wet electrode.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with an illustrative example, there is provided an apparatus to measure a bioimpedance, the apparatus including a first electrical signal generator configured to generate a first electrical signal to measure a bioimpedance of an object; a compensation signal generator configured to generate a compensation signal to compensate a biosignal measured based on the first electrical signal; and an amplifier configured to amplify the compensated biosignal.

The compensation signal may include a phase opposite to a phase of the biosignal, and an amplitude of the compensated biosignal may be smaller than an amplitude of the biosignal before the compensation.

The biosignal may be generated based on the first electrical signal and the bioimpedance.

The compensation signal generator may include a second electrical signal generator configured to generate a second electrical signal including a phase identical to or opposite to a phase of the first electrical signal.

The compensation signal generator may be configured to output the compensation signal generated in response to the second electrical signal flowing from electrodes into the object.

A distance between two electrodes applying the second electrical signal into the object may be shorter than a distance between two electrodes measuring the biosignal.

The compensation signal generator further may include an impedance element configured to generate the compensation signal based on the second electrical signal.

The compensation signal generator may be configured to adjust an amplitude of the second electrical signal based on an amplitude of the compensation signal.

The apparatus may also include a connection adjustor configured to adjust connections between electrodes electrically connected to the object, the first electrical signal generator, and the amplifier; and a controller configured to output a control signal to control a connection between switches included in the connection adjustor.

The connection adjustor may adjust, based on the control signal, connections among terminals connected to the electrodes, terminals connected to the first electrical signal generator, and terminals connected to the amplifier.

The apparatus may also include a first capacitor between an electrode, at which the biosignal is measured, and a node, at which the biosignal and the compensation signal are combined; and a second capacitor between a node, at which the compensation signal is output, and the node, at which the biosignal and the compensation signal are combined.

The apparatus may also include electrodes configured to conduct the first electrical signal or the biosignal to the object, and wherein at least one of the electrodes interfaces with the object in electrical regions.

The compensation signal generator may generate the compensation signal in response to the second electrical signal flowing through the object to compensate a biosignal generated based on the first electrical signal flowing through the object and based on an interface impedance between the object and electrodes.

In accordance with another illustrative example, there is provided an apparatus to measure a bioimpedance, the apparatus including an electrical signal generator configured to generate an electrical signal to measure a bioimpedance of an object; an amplifier configured to amplify a biosignal measured based on the electrical signal; and a connection adjustor configured to adjust connections between electrodes electrically connected to the object, the electrical signal generator, and the amplifier.

The connection adjustor may be configured to determine, among the electrodes, an electrode to which the electrical signal generated is transmitted based on a control signal.

In accordance with an illustrative example, there is provided a method of measuring a bioimpedance, the method including generating a first electrical signal to measure a bioimpedance of an object; generating a compensation signal to compensate for a biosignal generated based on the first electrical signal and the bioimpedance; and amplifying the compensated biosignal.

The compensated biosignal may include an amplitude smaller than an amplitude of the biosignal prior to compensation.

The outputting of the compensation signal may include generating a second electrical signal including a phase identical or opposite to a phase of the first electrical signal; and measuring a biosignal generated in response to the second electrical signal flowing into the object and thereby flowing in the object, and outputting the measured biosignal as the compensation signal.

A distance between two electrodes applying the second electrical signal to the object may be shorter than a distance between two electrodes measuring the biosignal.

The outputting of the compensation signal may include generating a second electrical signal including a phase identical or opposite to a phase of the first electrical signal; and outputting, as the compensation signal, an electrical signal generated in response to the second electrical signal flowing through an impedance element, and wherein the biosignal is combined with the compensation signal to decrease an amplitude of the biosignal.

Other features and aspects will be apparent from the following detailed description, the drawings, and the claims.

BRIEF DESCRIPTION OF THE DRAWINGS

These and/or other aspects will become apparent and more readily appreciated from the following description of the embodiments, taken in conjunction with the accompanying drawings in which.

Figure 1A:
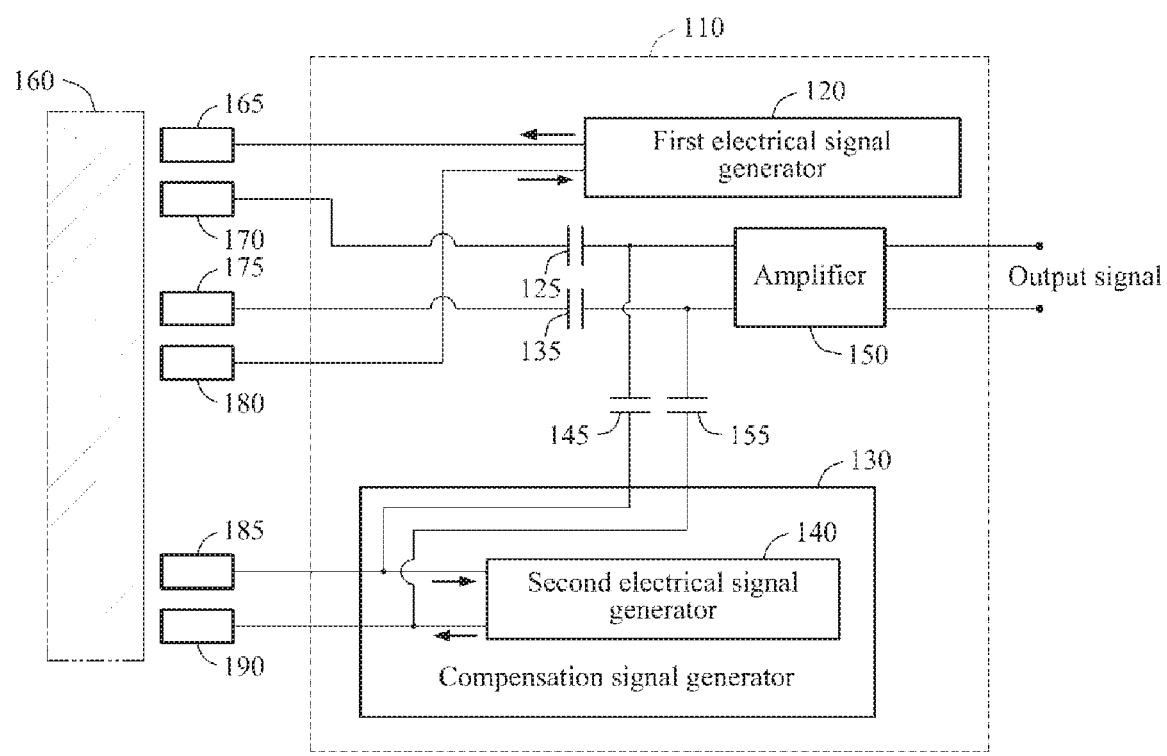
FIGS. 1A and 1B are diagrams illustrating an example of a configuration of a bioimpedance measuring apparatus, in accordance with an embodiment.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

It will be understood that when an element or layer is referred to as being "on" or "connected to" another element or layer, it can be directly on or connected to the other element or layer or through intervening elements or layers may be present. In contrast, when an element is referred to as being "directly on" or "directly connected to" another element or layer, there are no intervening elements or layers present. Like reference numerals refer to like elements throughout. As used herein, the term "and/or" includes any and all combinations of one or more of the associated listed items.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1B:
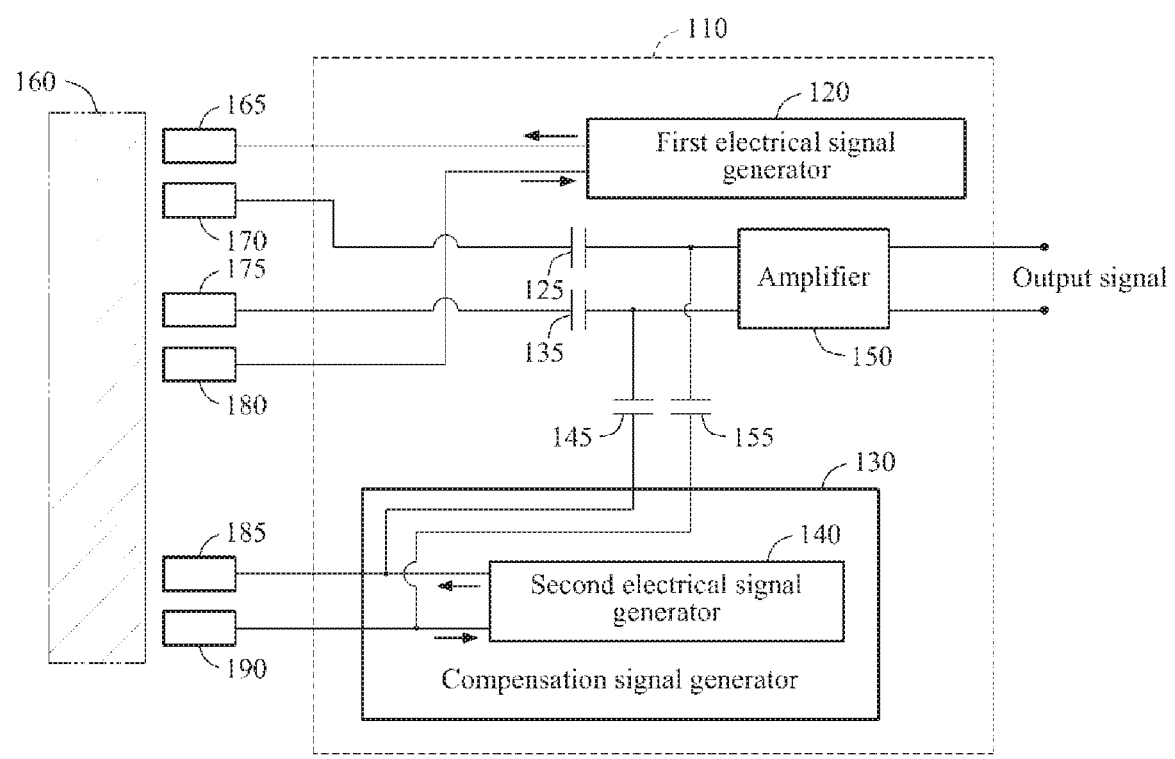

FIGS. 1A and 1B are diagrams illustrating an example of a configuration of a bioimpedance measuring apparatus 110, in accordance with an embodiment. The bioimpedance measuring apparatus 110 illustrated in FIGS. 1A and 1B measure a bioimpedance of an object 160. The object 160 may include a human or animal organ, tissue, muscle, veins, or other portion of a human body or animal body. A type of the bioimpedance may vary. For example, the bioimpedance includes a bioimpedance indicating a resistance degree in the skin, a bioimpedance indicating a hydration degree of the skin, a bioimpedance that varies depending on pulmonary respiration, a bioimpedance that varies depending on blood flow, a bioimpedance present on an electrical path through the skin and a measurement electrode, a bioimpedance indicating an activation degree of a sympathetic nerve, and the like.

The bioimpedance measured by the bioimpedance measuring apparatus 110 may be used to estimate a body fat content of the object 160. The bioimpedance measuring apparatus 110 may be implemented in a variety of wearable devices. For example, the bioimpedance measuring apparatus 110 may be included in a wearable device such as a watch, a glove, clothing, a hat, or a shoe. The bioimpedance measuring apparatus 110 converts the measured bioimpedance to biodata suitable for the wearable device to process and transmits the converted bioimpedance to the wearable device. The wearable device then analyzes the body fat components of the object 160 based on the biodata received from the bioimpedance measuring apparatus 110 and provides a result of the analyzing to a user.

In an example, to measure the bioimpedance, the bioimpedance measuring apparatus 110 applies, using an electrode, a current signal having a frequency component to the object 160, for example, a body of the user. Using another electrode, the bioimpedance measuring apparatus 110 measures a voltage signal generated in response to the current signal flowing into the object 160 and thereby flowing through the object 160. For example, using an electrode, the bioimpedance measuring apparatus 110 applies an alternating current (AC) signal having a frequency component between a kilohertz (kHz) and 1 megahertz (MHz) to skin of the user to measure the bioimpedance. Using another electrode, the bioimpedance measuring apparatus 110 measures an AC voltage signal generated by the AC signal and the bioimpedance. The bioimpedance of the object 160 is estimated based on the current signal applied to the object 160 and the voltage signal measured from the object 160.

In another example, to measure a bioimpedance, the bioimpedance measuring apparatus 110 applies, using an electrode, a voltage signal having a frequency component to the object 160. Using another electrode, the bioimpedance measuring apparatus 110 measures a current signal generated in response to the voltage signal flowing through the object 160. The bioimpedance of the object 160 is estimated based on the voltage signal applied to the object 160 and the current signal measured from the object 160.

In measuring an electrical signal from the object 160 using an electrode, the electrical signal to be measured may be affected by an interface impedance, which is an impedance generated from an interface between the electrode and skin and/or organ of the user. For example, a dry electrode that measures a biosignal without using an electrolyte such as a gel may have an interface impedance greater or considerably greater than a bioimpedance to be measured. The dry electrode includes, for example, a metal electrode, a conductive rubber electrode, and a capacitive coupling electrode. In general, a magnitude of the bioimpedance to be measured is approximately several hundred ohms. As a result, a measurement resolution that distinguishes an impedance difference of approximately 0.5 ohm may be required. The dry electrode generally has an interface impedance of greater than or equal to 1 kilo ohm.

As a magnitude of the interface impedance between the electrode and the skin of the user increases, a magnitude of the electrical signal to be measured from the object 160 also increases. An amplifier 150 that amplifies the biosignal, which is the converted measured bioimpedance of the object 160 that is based on the voltage signal applied to the object 160 and the current signal measured from the object 160, has a range of input electrical signals that can be amplified. The biosignal may be measured in a form of a voltage signal or a current signal, and include bioimpedance information.

When the measured biosignal is input to the amplifier 150, without being adjusted, the biosignal deviating from an operational range of the amplifier 150 is input to the amplifier 150. A magnitude of the biosignal is greater than the operation range of the amplifier 150 due to the magnitude of the interface impedance. To offset a factor that may be caused by the interface impedance on the biosignal measured from the object 160, the bioimpedance measuring apparatus 110 compensates the biosignal prior to being input to the amplifier 150 using a compensation signal. Thus, the compensation signal decreases an amplitude of the biosignal input to the amplifier 150 is decreased, within the operational range of the amplifier 150. Accordingly, the bioimpedance measuring apparatus 110 prevents saturation of the amplifier 150 caused by an input of a biosignal measured from the object 160 having a magnitude or an amplitude exceeding the operational range of the amplifier 150 due to interface impedance. The bioimpedance measuring apparatus 110 measures a bioimpedance and compensates the biosignal.

In addition, the bioimpedance measuring apparatus 110 compensates the biosignal measured from the object 160 and decreases the magnitude of the biosignal to enable a use of an analog-to-digital converter (ADC) having a lower measurement resolution. The ADC disposed at a signal processing terminal converts the biosignal amplified by the amplifier 150 to a digital signal. When all impedances on a path through which a bioimpedance is measured are smaller, a signal-to-noise ratio (SNR) required in the measurement circuit increases, and an effective number of bits (ENOB) required in the ADC decreases. The bioimpedance measuring apparatus 110 reduces a magnitude of the all bioimpedances calculated on the path by reducing a magnitude of the biosignal measured from the object 160, and enables usage of a lower resolution ADC.

The magnitude of the interface impedance between the electrode and the skin of the user may vary depending on the number of users. Also, the magnitude of the interface impedance may vary depending on measuring environments, for example, a skin moisture level, a surface area of an electrode, a temperature, and a pressure applied to an electrode. The bioimpedance measuring apparatus 110 precisely measures a bioimpedance by decreasing an influence of the interface impedance sensitivity on the biosignal measured from the object 160.

Referring to FIG. 1A, the bioimpedance measuring apparatus 110 includes a first electrical signal generator 120, a compensation signal generator 130, and the amplifier 150.

The first electrical signal generator 120 generates a first electrical signal to measure a bioimpedance of the object 160. For example, the first electrical signal is an AC signal or an AC voltage signal having a frequency component. The first electrical signal generated by the first electrical signal generator 120 is applied to the object 160 through electrodes, for example, electrodes 165 and 180. An electrical path is formed between the first electrical signal generator 120, the object 160, and the electrodes 165 and 180. The first electrical signal applied to the object 160 flows through the formed electrical path. Thus, a biosignal is generated based on the first electrical signal flowing in the object 160 and the bioimpedance. The generated biosignal is measured through electrodes, for example, electrodes 170 and 175.

The electrodes 165, 170, 175, and 180 provide an interface between the first electrical signal, the biosignal, and the object 160. In an example, at least one of the electrodes 165, 170, 175, and 180 interfaces with the object 160 in electrical regions. Also, the electrode 165 and the electrode 170 may include sub-electrodes having respective electrical regions, and the sub-electrodes of the electrode 165 and the electrode 170 may be disposed in a mixed form, in a matrix form, in sequential form, or in parallel form. A detailed description will be provided with reference to FIGS. 5 and 6.

The compensation signal generator 130 generates a compensation signal to compensate for the biosignal measured based on the first electrical signal. The compensation signal has a phase opposite to a phase of the biosignal, and an amplitude of the biosignal being compensated for by the compensation signal is smaller than an amplitude of the compensation signal. The compensation signal generator 130 uses an interface impedance between the object 160 and electrodes, for example, 185 and 190, to generate the compensation signal.

As illustrated in FIG. 1A, the compensation signal generator 130 includes a second electrical signal generator 140. The second electrical signal generator 140 generates a second electrical signal having a phase opposite to a phase of the first electrical signal or a phase difference of 180 degrees (°) from the phase of the first electrical signal. The second electrical signal may be an AC signal having a frequency component identical to the first electrical signal. The second electrical signal is applied to the object 160 through the electrodes 185 and 190. The second electrical signal generator 140, the electrode 185, the object 160, and the electrode 190 form an electrical path where the second electrical signal applied to the object 160 flows through the formed electrical path. The compensation signal is generated in response to the second electrical signal flowing into the object 160 and thereby flowing through the object 160. Also, the compensation signal is generated in response to the second electrical signal flowing through the interface impedance between the object 160 and the electrodes 185 and 190. The compensation signal generator 130 outputs, as the compensation signal, a signal generated in response to the second electrical signal flowing into the object 160 through the electrodes 185 and 190.

In an example, the first electrical signal and the second electrical signal are current signals, and the biosignal and the compensation signal are voltage signals. Conversely, in another example, the first electrical signal and the second electrical signal are voltage signals, and the biosignal and the compensation signal are current signals.

The electrodes 185 and 190 applying the second electrical signal to the object 160 are disposed in close proximity to each other. To maximize an influence of the interface impedance between the object 160 and the electrodes 185 and 190 and minimize an influence of the bioimpedance, a distance between the electrodes 185 and 190 applying the second electrical signal to the object 160 is designed to be shorter than a distance between the two electrodes 170 and 175 measuring the biosignal from the object 160.

The compensation signal is combined with the biosignal at an input terminal of the amplifier 150. The biosignal is combined with the compensation signal to decrease an amplitude of the biosignal by an amplitude of the compensation signal. The biosignal being compensated for by the compensation signal or a signal obtained by combining the biosignal and the compensation signal is referred to as a combination signal. The amplitude of the biosignal decreases by combining the biosignal and the compensation signal due to the biosignal and the compensation signal having opposite phases. The biosignal being compensated for by the compensation signal includes, in one example, only an electrical signal with a bioimpedance factor because an interface impedance factor almost identical to an interface impedance factor between the object 160 and the electrodes 170 and 175 is reflected in the compensation signal.

As illustrated in FIG. 1A, first capacitors, for example, 125 and 135, are disposed between the electrodes 170 and 175 at which the biosignal is measured and nodes at which the biosignal and the compensation signal are combined. In addition, second capacitors, for example, 145 and 155, are disposed between nodes at which the compensation signal is output and the nodes at which the biosignal and the compensation signal are combined.

The compensation signal generator 130 adjusts the amplitude of the second electrical signal output from the second electrical signal generator 140 based on the amplitude of the compensation signal. Due to a measuring environment between the electrodes 170 and 175, and the object 160 including noise and ambient and structural resistances, a magnitude of an interface impedance generated between the object 160 and the electrodes 170 and 175 at which the biosignal is measured may differ from a magnitude of an interface impedance generated between the object 160 and the electrodes 185 and 190 at which the compensation signal is generated. In addition, the magnitude of the interface impedance generated between the object 160 and the electrodes 185 and 190 may vary at each point in time during measurement.

The amplitude of the compensation signal increases in proportion to the magnitude of the interface impedance generated between the object 160 and the electrodes 185 and 190 and to the amplitude of the second electrical signal. When the amplitude of the compensation signal is determined to be higher than a predetermined threshold range, the compensation signal generator 130 decreases the amplitude of the compensation signal by decreasing the amplitude of the second electrical signal output from the second electrical signal generator 140. Conversely, when the amplitude of the compensation signal is determined to be lower than the predetermined threshold range, the compensation signal generator 130 increases the amplitude of the compensation signal by increasing the amplitude of the second electrical signal output from the second electrical signal generator 140.

The combination signal of the biosignal and the compensation signal is input to the amplifier 150, and the amplifier 150 amplifies the combination signal. In one illustrative example, the combination signal is input to the amplifier 150 in a form of a differential signal. For example, an instrumentation amplifier (IA) that is widely used to amplify a biosignal is used as the amplifier 150. The bioimpedance measuring apparatus 110 outputs the amplified combination signal as an output signal.

In an example, the output signal from the amplifier 150 is demodulated. A control signal used to demodulate the output signal has a frequency component used by the first electrical signal generator 120, and has a signal with or without a phase difference, as necessary. The output signal from the bioimpedance measuring apparatus 110 passes through post-processing, for example, filtering, and an analog-to-digital converter (ADC) converts the output signal to a digital signal. Thus, the bioimpedance of the object 160 is estimated by analyzing a digital signal. The estimated bioimpedance of the object 160 is then provided to the user through a display device. The display device is a structural device configured to output a numerical estimate of the bioimpedance of the object 160. The display device includes, but is not limited to, a liquid crystal display, a plasma display, a mobile phone, a tablet, or other similar display devices.

In another example, as illustrated in FIG. 1B, the second electrical signal generator 140 generates a second electrical signal having a phase identical to a phase of the first electrical signal. The second electrical signal is an AC signal or an AC voltage signal having a frequency component and the phase identical to the first electrical signal. The second electrical signal is applied to the object 160 through the electrodes 185 and 190. The second electrical signal applied to the object 160 generates the compensation signal, and the compensation signal is combined with the biosignal. In FIG. 1B, a connection between the node at which the compensation signal is output and a signal line through which the biosignal is transmitted is opposite to a corresponding connection illustrated in FIG. 1A. Also in FIG. 1B, the amplitude of the biosignal decreases when the biosignal is combined with the compensation signal having the phase opposite to the phase of the biosignal. Descriptions other than the foregoing may be the same as descriptions provided with reference to FIG. 1A.

Figure 2:
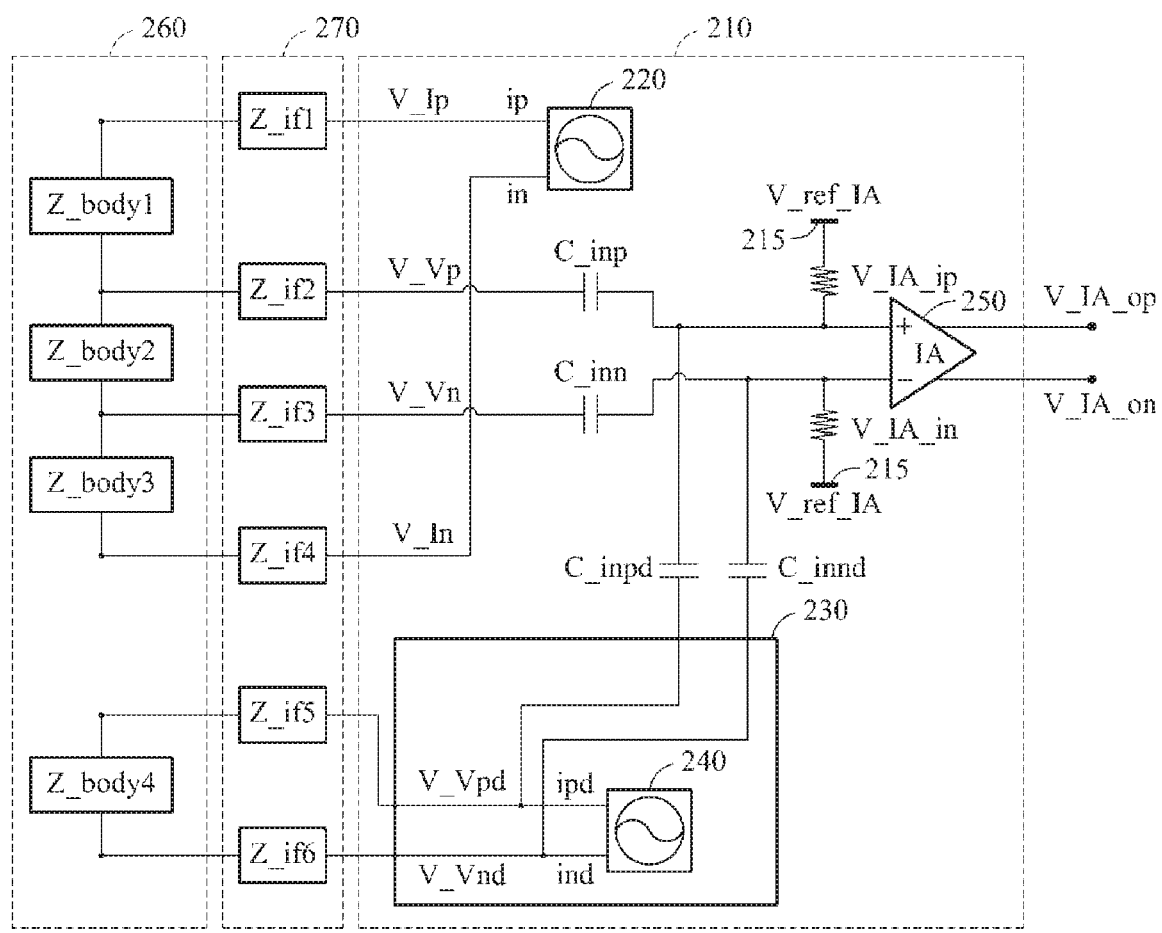
FIG. 2 is a diagram illustrating an example of an operation of the bioimpedance measuring apparatus, in accordance with an embodiment.

FIG. 2 is a diagram illustrating an example of an operation of a bioimpedance measuring apparatus 210, in accordance with an embodiment. Referring to FIG. 2, the bioimpedance measuring apparatus 210 includes a first electrical signal generator 220, a compensation signal generator 230, and an amplifier 250. The compensation signal generator 230 includes a second electrical signal generator 240.

The first electrical signal generator 220 generates a first electrical signal, "ip" and "in," to measure a bioimpedance. The generated first electrical signal is applied to an object, for example, a body of a user, through electrodes. An interface impedance may be generated between the object and an electrode. As illustrated in FIG. 2, "Z_jf1" through "Z_jf6" indicate an equivalent model 270 of the interface impedance generated between the object and each electrode. "Z_body1" through "Z_body4" indicate an equivalent model 260 of a bioimpedance of the object, and "Z_body2" among Z_body1 through Z_body4 indicates a desired bioimpedance to be measured. The biosignal is generated based on the first electrical signal and the measured bioimpedance Z_body2. The first electrical signal is output in a form of a current signal or a voltage signal. In one configuration, a voltage difference between a node "V_Vp" and a node "V_Vn" at which the biosignal is measured has a very large value due to the interface impedance, Z_if1 through Z_if4, having a large impedance value.

The compensation signal generator 230 generates a compensation signal to decrease an amplitude of the biosignal. The second electrical signal generator 240, in the compensation signal generator 230, generates a second electrical signal, "ipd" and "ind," having a phase identical or opposite to a phase of the first electrical signal. Identically to the first electrical signal, the second electrical signal is output in a form of a current signal or a voltage signal. Based on the phase of the second electrical signal, a combination relationship between the biosignal and the compensation signal is different, and a detailed description may be found with reference to FIGS. 1A and 1B. The second electrical signal generated by the second electrical signal generator 240 is applied to the object through an electrode.

As illustrated in FIG. 2, "Z_if5" and "Z_if6" indicate an equivalent model of an interface impedance generated between the object and electrodes applying the second electrical signal to the object. "Z_body4" indicates a bioimpedance on a path through which the second electrical signal flows. The compensation signal generated based on the second electrical signal, the interface impedance Z_if5 and Z_jf6, and the bioimpedance Z_body4 is output from a node "V_Vpd" and a node "V_Vnd."

The biosignal and the compensation signal are combined at an input terminal of the amplifier 250. The compensation signal decreases an amplitude of the biosignal. Because the amplitude of a combination signal of the biosignal and the compensation signal is smaller than the amplitude of the biosignal and the amplitude of the compensation signal, the amplifier 250 is less likely to be saturated by the combination signal of the biosignal and the compensation signal. Thus, despite a large value of the interface impedances Z_if1 through Z_if4, the bioimpedance measuring apparatus 210 amplifies the biosignal including bioimpedance information without saturating the amplifier 250. In FIG. 2, "V_ref_IA" 215 indicates a reference signal used to determine a direct current (DC) signal component of the input signal to the amplifier 250.

Figure 3:
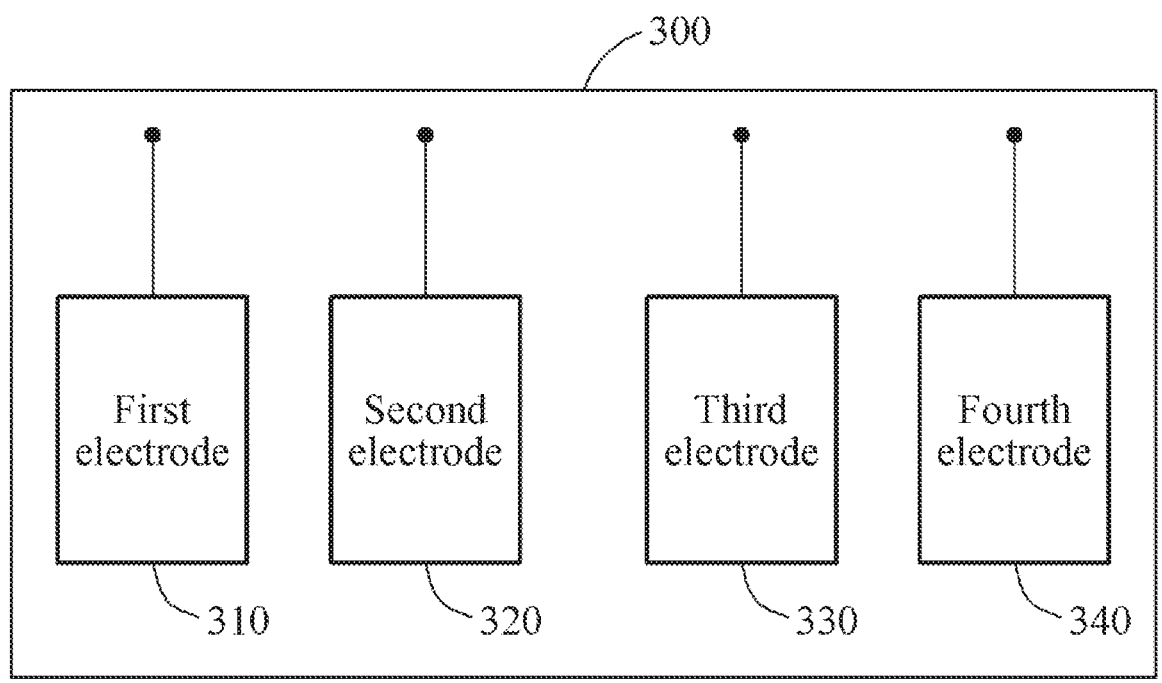
FIGS. 3 and 4 are diagrams illustrating examples of bioelectrodes, in accordance with an embodiment.
Figure 4:
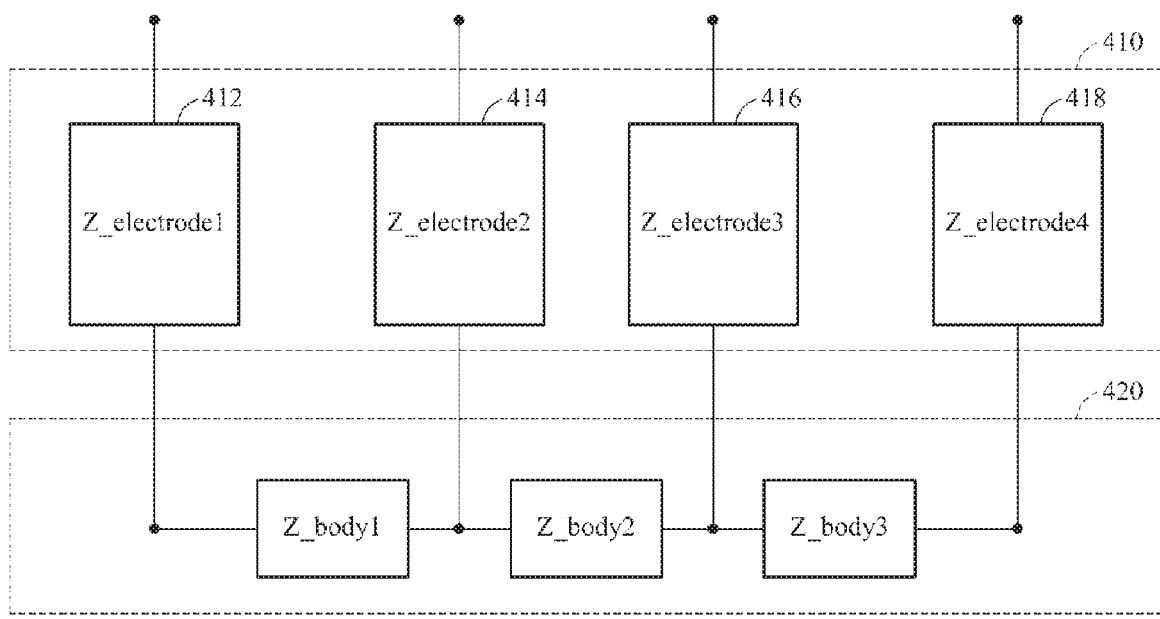

FIGS. 3 and 4 are diagrams illustrating an example of bioelectrodes, in accordance with an embodiment.

FIG. 3 is a diagram illustrating an example of a bioelectrode 300 including electrodes, for example, a first electrode 310, a second electrode 320, a third electrode 330, and a fourth electrode 340, that apply a first electrical signal to an object or measure a biosignal from the object.

Referring to FIG. 3, the first electrode 310, the second electrode 320, the third electrode 330, and the fourth electrode 340 correspond to the electrode 165, the electrode 170, the electrode 175, and the electrode 180 illustrated in FIGS. 1A and 1B, respectively. The electrodes 310 through 340 are made of a conductive material, and are wet electrodes or dry electrodes. Alternatively, the electrodes 310 through 340 are capacitive coupling electrodes that measure a biosignal with a contact surface with the object being insulated. Each electrode of the bioelectrode 300 has one electrical region.

FIG. 4 is a diagram illustrating electrically equivalent models between the electrodes 310 through 340 illustrated in FIG. 3 and the object to which the electrodes 310 through 340 are attached. Referring to FIG. 4, "Z_electrode1" 412 through "Z_electrode4" 418 are an equivalent model 410 of an interface impedance generated between the object and each of the electrodes 310 through 340. "Z_body1" through "Z_body 3" are an equivalent model 420 of a bioimpedance of the object, and "Z_body2" among Z_body1 through Z_body 3 are a desired bioimpedance to be measured.

In FIG. 4, Z_electrode1 412 and Z_electrode2 414 have different values based on a contact between the electrodes. Similarly, Z_electrode3 416 and Z_electrode4 418 have different values based on a contact between the electrodes. Thus, when measuring the bioimpedance Z_body2 using the electrodes, a value to be measured may be greatly affected by the contact between the electrodes.

Figure 5:
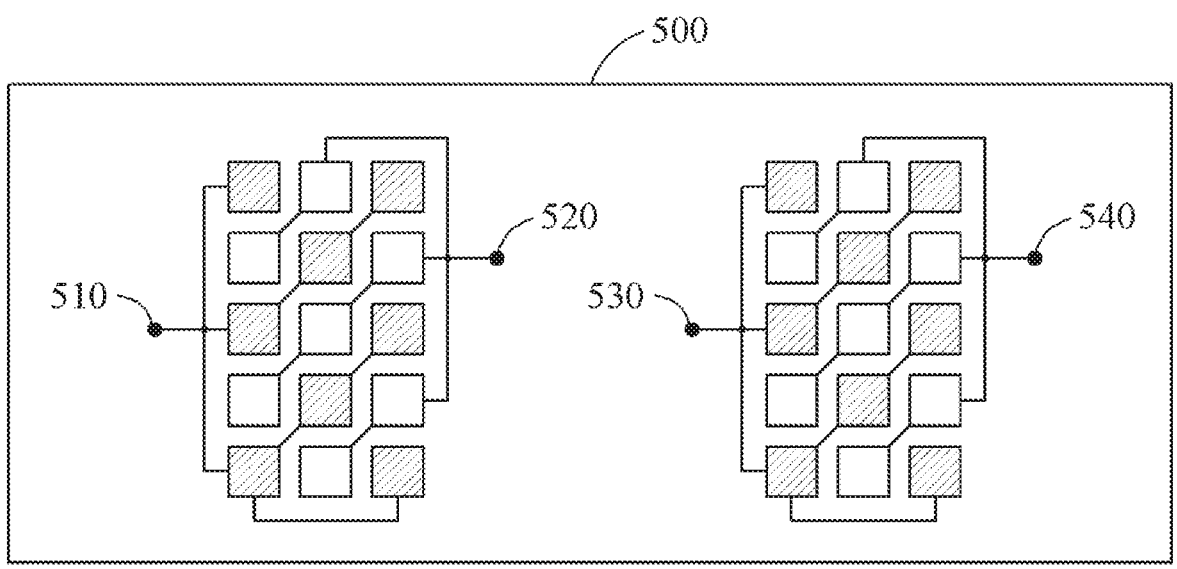
FIGS. 5 and 6 are diagrams illustrating examples of other bioelectrodes, in accordance with an embodiment.
Figure 6:
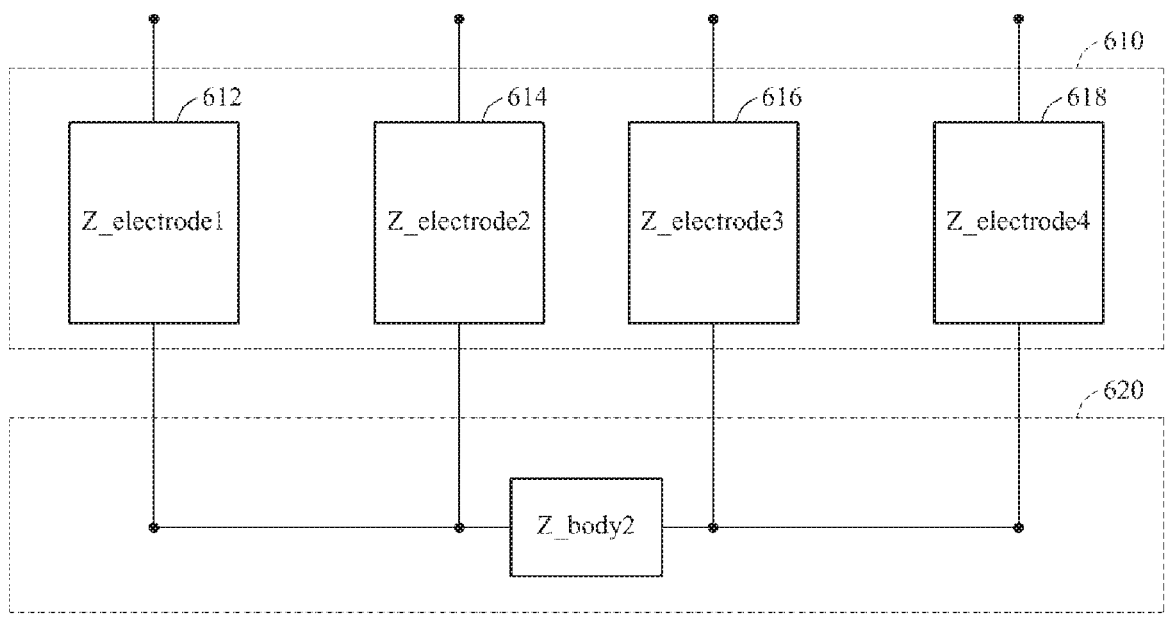

FIGS. 5 and 6 are diagrams illustrating example of other bioelectrodes, in accordance with an embodiment.

FIG. 5 is a diagram illustrating an example of a bioelectrode 500 including electrodes, for example, a first electrode 510, a second electrode 520, a third electrode 530, and a fourth electrode 540, that apply a first electrical signal to an object or measure a biosignal from the object.

Referring to FIG. 5, the first electrode 510, the second electrode 520, the third electrode 530, and the fourth electrode 540 correspond to the electrode 165, the electrode 170, the electrode 175, and the electrode 180 illustrated in FIGS. 1A and 1B, respectively. The electrodes 510 through 540 are made of a conductive material, and are wet or dry electrodes. Alternatively, the electrodes 510 through 540 are capacitive coupling electrodes that measure a biosignal with a contact surface with the object being insulated.

Dissimilar to the bioelectrode 300 of FIG. 3, each of the electrodes 510 through 540 of the bioelectrode 500 have electrical regions. The electrical regions of each electrode are electrically connected to one another.

An electrode may be attached to a portion of body skin of a user to measure a biosignal including a bioimpedance. The entire electrode or a portion thereof may be in contact with the skin. Thus, in the bioelectrode 300 of FIG. 3, the first electrode 310 and the second electrode 320 may be in contact with the skin at different locations. Also, different electrical conditions may be formed between the first electrode 310 and the second electrode 320.

However, in the bioelectrode 500 of FIG. 5, the first electrode 510 and the second electrode 520 include sub-electrodes having respective electrical regions, and sub-electrodes of the first electrode 510 and sub-electrodes of the second electrode 520 are disposed in a mixed form. In one alternative configuration, the sub-electrodes of the first electrode 510 and sub-electrodes of the second electrode 520 are disposed in a series form, a parallel form, or a sequential form. Due to such an electrode structure, conditions for contact between the first electrode 510 and the skin and conditions for contact between the second electrode 520 and the skin may become considerably identical and; as a result, a biosignal can be precisely measured. Similarly, the third electrode 530 and the fourth electrode 540 include sub-electrodes having respective electrical regions, and sub-electrodes of the third electrode 530 and sub-electrodes of the fourth electrode 540 are disposed in a mixed form. In one alternative configuration, the sub-electrodes of the third electrode 530 and sub-electrodes of the fourth electrode 540 are disposed in a series form, a parallel form, or a sequential form.

FIG. 6 is a diagram illustrating electrically equivalent models between the electrodes 510 through 540 illustrated in FIG. 5 and the object to which the electrodes 510 through 540 are attached, in accordance with an embodiment. Referring to FIG. 6, "Z_electrode1" 612 through "Z_electrode4" 618 are an equivalent model 610 of an interface impedance generated between each of the electrodes 510 through 540 and the object. Also, "Z_body2" is an equivalent model 620 of a bioimpedance of the object, and "Z_body2" is a desired bioimpedance to be measured.

Due to the electrode structure, the first electrode 510 and the second electrode 520 of FIG. 5 may have identical conditions for contact and; thus, "Z_electrode1" 612 and "Z_electrode2" 614 may be identical. Similarly, due to the electrode structure, the third electrode 530 and the fourth electrode 540 of FIG. 5 may have identical conditions for contact and; thus, "Z_electrode3" 616 and "Z_electrode4" 618 may be identical.

In a case that Z_electrode1 612 and Z_electrode2 614 are identical, values of Z_electrode1 612 and Z_electrode2 614 are estimated by applying a current signal to the object, such as the object 160 illustrated in FIG. 1A, through a node of the first electrode 510 and a node of the second electrode 520 and measuring a difference in voltage signals to be generated. Similarly, in a case that Z_electrode3 616 and Z_electrode4 618 are identical, values of Z_electrode3 616 and Z_electrode4 618 are estimated by applying a current signal to the object through a node of the third electrode 530 and a node of the fourth electrode 540 and measuring a difference in voltage signals to be generated. Subsequently, a summed value of Z_electrode2 614, Z_body2, and Z_electrode3 616 (Z_electrode2+Z_body2+Z_electrode3) is estimated by applying a current signal to the object through the node of the first electrode 510 and the node of the fourth electrode 540 and measuring voltage signals through the node of the second electrode 520 and the node of the third electrode 530. In such an example, values of Z_electrode2 614 and Z_electrode3 616 are previously estimated and known. Therefore, a value of Z_body2 is calculated based on a sum of (Z_electrode2+Z_body2+Z_electrode3).

Figure 7A:
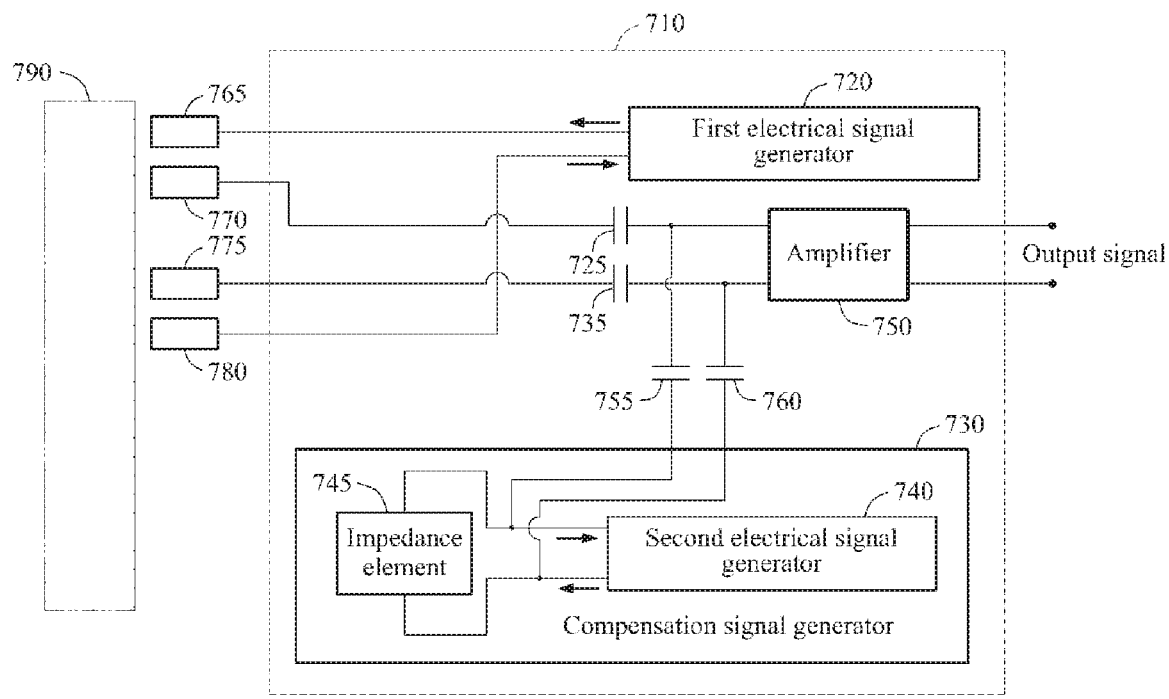
FIGS. 7A and 7B are diagrams illustrating another example of a configuration of a bioimpedance measuring apparatus, in accordance with an embodiment.
Figure 7B:
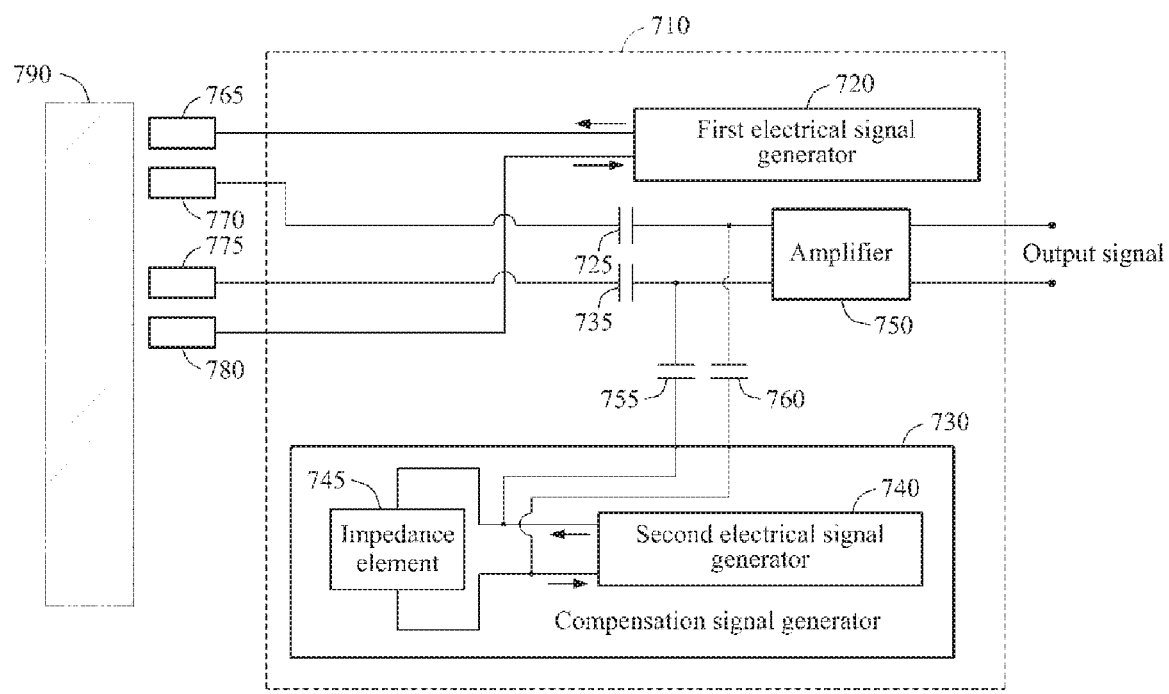

FIGS. 7A and 7B are diagrams illustrating another example of a configuration of a bioimpedance measuring apparatus 710, in accordance with an embodiment. Referring to FIG. 7A, the bioimpedance measuring apparatus 710 includes a first electrical signal generator 720, a compensation signal generator 730, and an amplifier 750. The compensation signal generator 730 includes a second electrical signal generator 740 and an impedance element 745.

The first electrical signal generator 720 generates a first electrical signal to measure a bioimpedance of an object 790. The first electrical signal is an AC signal or an AC voltage signal having a frequency component. The first electrical signal generated by the first electrical signal generator 720 is applied to the object 790 through electrodes, for example, electrodes 765 and 780. The first electrical signal generator 720 and the electrodes 765 and 780 form an electrical path for the first electrical signal to flow through the object 790. A biosignal may then be generated based on the first electrical signal flowing through the object 790 and the bioimpedance of the object 790. The biosignal is measured through electrodes, for example, 770 and 775.

The compensation signal generator 730 generates a compensation signal to compensate for the biosignal. The compensation signal has a phase opposite to a phase of the biosignal. An amplitude of the biosignal being compensated for by the compensation signal is smaller than an amplitude of the compensation signal. The compensation signal generator 730 generates the compensation signal based on a second electrical signal generated at the second electrical signal generator 740. The second electrical signal generator 740 generates the second electrical signal having a phase opposite to a phase of the first electrical signal or a phase difference of 180° from the first electrical signal. The second electrical signal may be an AC signal or an AC voltage signal having a frequency component identical to the first electrical signal.

The compensation signal generator 730 generates the compensation signal based on the second electrical signal generated at the second electrical signal generator 740 and the impedance element 745. The compensation signal is generated in response to the second electrical signal flowing through the impedance element 745. In one example, the impedance element 745 may have an impedance value of a predetermined magnitude. In one example, the impedance value of the impedance element 745 is designed to be similar to a value of an interface impedance between the electrodes and the object 790. A passive device, for example, a resistor and a capacitor, may be used as the impedance element 745.

The compensation signal output from the compensation signal generator 730 is combined with the biosignal at an input terminal of the amplifier 750. As a result of the combination of the biosignal and the compensation signal, the amplitude of the biosignal decreases by the amplitude of the compensation signal. The amplitude of the biosignal decreases through the combination of the biosignal and the compensation signal having opposite phases.

As illustrated in FIG. 7A, first capacitors, for example, 725 and 735, are disposed between the electrodes 770 and 775 at which the biosignal is measured and nodes at which the biosignal and the compensation signal are combined. Also, second capacitors, for example, 755 and 760, are disposed between nodes at which the compensation signal is output and the nodes at which the biosignal and the compensation signal are combined.

The compensation signal generator 730 adjusts an amplitude of the second electrical signal output from the second electrical signal generator 740 based on the amplitude of the compensation signal. In one illustrative example, the amplitude of the compensation signal increases in proportion to the amplitude of the second electrical signal and the impedance value of the impedance element 745. When the amplitude of the compensation signal is determined to be higher than a predetermined threshold range, the compensation signal generator 730 decreases the amplitude of the compensation signal by decreasing the amplitude of the second electrical signal output from the second electrical single generator 740. Conversely, when the amplitude of the compensation signal is determined to be lower than the predetermined threshold range, the compensation signal generator 730 increases the amplitude of the compensation signal by increasing the second electrical signal output from the second electrical signal generator 740.

A combination signal of the biosignal and the compensation signal are input to the amplifier 750. The amplifier 750 amplifies the combination signal. The bioimpedance measuring apparatus 710 outputs the amplified combination signal as an output signal. The bioimpedance measuring apparatus 710 processes a signal having a greater level by decreasing an amplitude of an input signal input to the amplifier 750 and amplifying the signal with the decreased amplitude. In addition, the bioimpedance measuring apparatus 710 improves accuracy in the measurement of a bioimpedance by reducing an influence of an interface impedance value that varies with objects or at each point in time of measurement.

Referring to FIG. 7B, the second electrical signal generator 740 generates a second electrical signal having a phase identical to a phase of a first electrical signal. The second electrical signal is an AC signal or an AC voltage signal having a frequency component and a phase identical to the first electrical signal. A compensation signal is generated in response to the second electrical signal flowing through the impedance element 745. The compensation signal is input to the amplifier 750 subsequent to being combined with a biosignal. In FIG. 7B, a connection between a node at which the compensation signal is output and a signal line through which the biosignal is transmitted is opposite to a corresponding connection illustrated in FIG. 7A. Also, in FIG. 7B, an amplitude of the biosignal decreases when the biosignal and the compensation signal have a phase opposite to a phase of the biosignal are combined. Descriptions other than the foregoing may be the same as descriptions provided with reference to FIG. 7A and; thus, repeated descriptions shall be omitted for conciseness.

Figure 8:
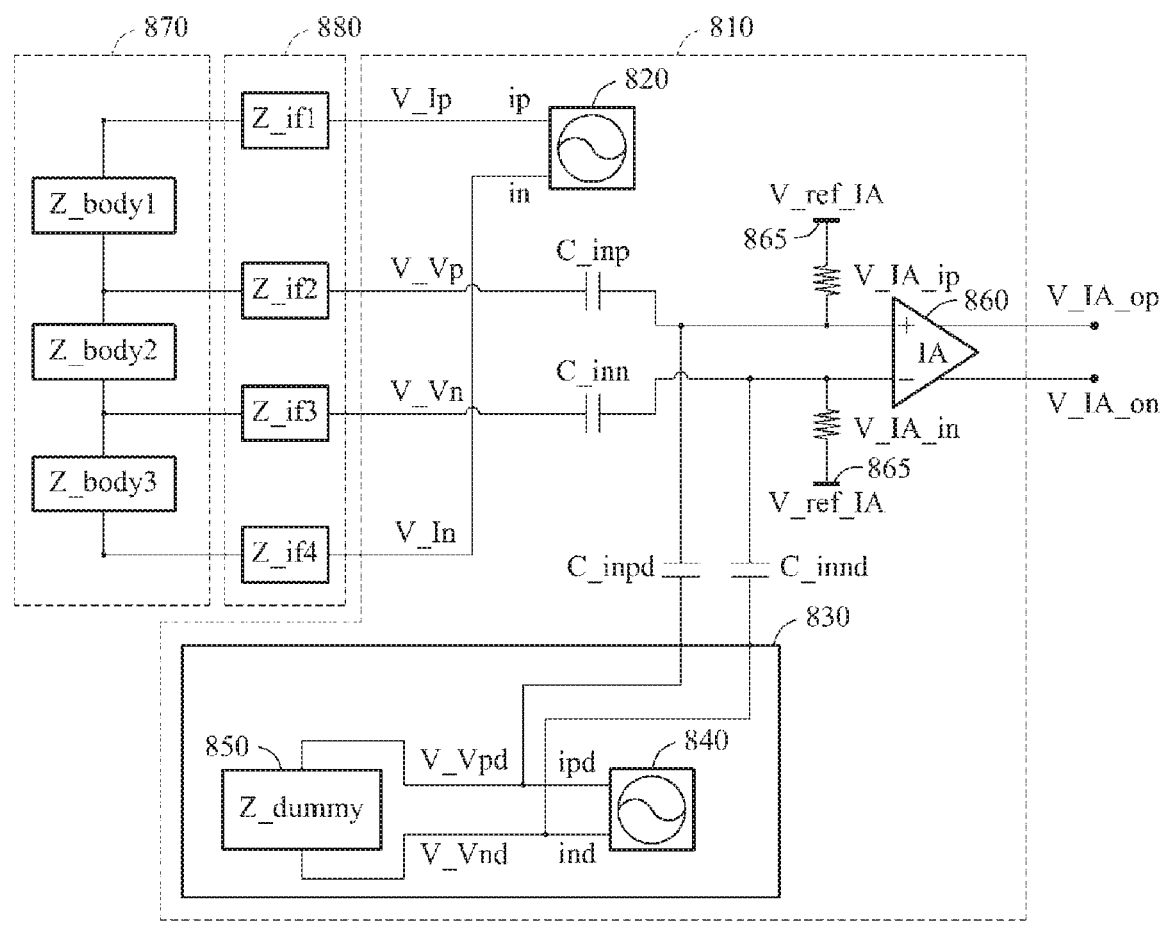
FIG. 8 is a diagram illustrating another example of an operation of the bioimpedance measuring apparatus, in accordance with an embodiment.

FIG. 8 is a diagram illustrating another example of an operation of a bioimpedance measuring apparatus 810, in accordance with an embodiment. Referring to FIG. 8, the bioimpedance measuring apparatus 810 includes a first electrical signal generator 820, a compensation signal generator 830, and an amplifier 860. The compensation signal generator 830 includes a second electrical signal generator 840 and an impedance element, "Z_dummy," 850.

The first electrical signal generator 820 generates a first electrical signal, for example, "ip" and "in," to measure a bioimpedance of an object. The generated first electrical signal is applied to the object through a plurality of electrodes. "Z_if1" through "Z_if4" are an equivalent model 880 of an interface impedance generated between the electrodes and the object. "Z_body1" through "Z_body3" are an equivalent model 870 of a bioimpedance of the object, and "Z_body2" among Z_body1 through Z_body3 indicates a desired bioimpedance to be measured. A biosignal is generated based on the first electrical signal and the bioimpedance Z_body2 to be actually measured. A voltage difference between a node "V_Vp" and a node "V_Vn" at which the biosignal is measured may have a considerably large value due to the interface impedance Z_if1 through Z_if4 having a large impedance value.

The compensation signal generator 830 generates a compensation signal to decrease an amplitude of the biosignal. The second electrical signal generator 840 included in the compensation signal generator 830 generates a second electrical signal, for example, "ipd" and "inp," having a phase identical or opposite to a phase of the first electrical signal. Based on the phase of the second electrical signal, a combination relationship between the biosignal and the compensation signal may vary. A detailed description of the combination relationship between the biosignal and the compensation signal is found with reference to FIGS. 7A and 7B. The second electrical signal generated by the second electrical signal generator 840 flows through both terminals of the impedance element Z_dummy 850. The impedance of the element Z_dummy 850 and the second electrical signal generate the compensation signal. The compensation signal is output from a node "V_Vpd" and a node "V_Vnd." The impedance element Z_dummy 850 may have an impedance value corresponding to the interface impedance Z_if1 through Z_jf4.

The biosignal and the compensation signal are combined at an input terminal of the amplifier 860. As a result, the compensation signal decreases the amplitude of the biosignal. The amplifier 860 amplifies a combination signal of the biosignal and the compensation signal. In FIG. 8, "V_ref_IA" 865 indicates a reference signal used to determine a DC signal component of an input signal to the amplifier 860.

Figure 9:
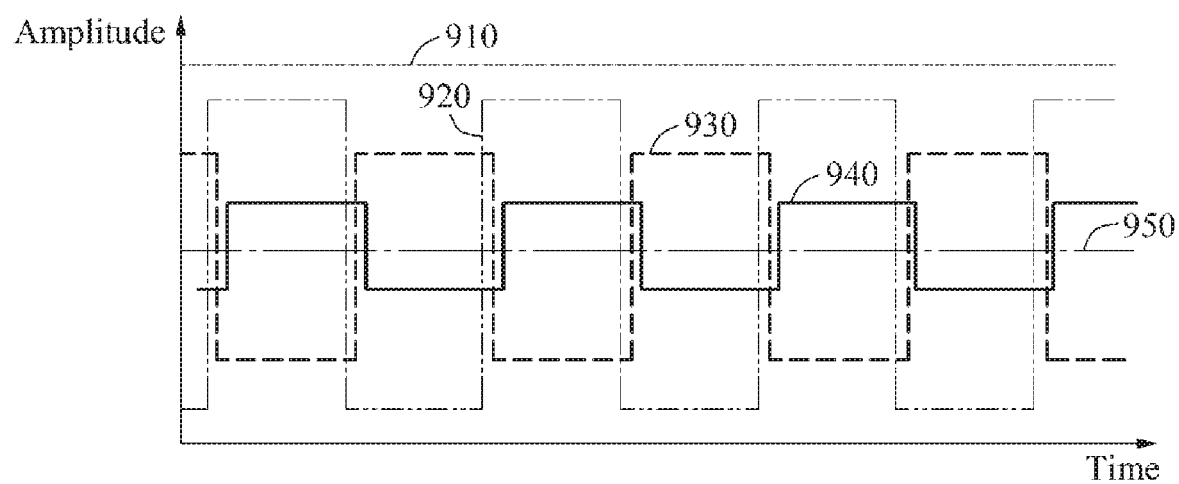
FIG. 9 is a diagram illustrating, using a signal waveform, an example of a process in which a compensation signal compensates a biosignal measured from an object, in accordance with an embodiment.

FIG. 9 is a diagram illustrating, using a signal waveform, an example of a process in which a compensation signal compensates a biosignal measured from an object, in accordance with an embodiment. Referring to a graph of FIG. 9, a first reference line 910 indicates a level of an input signal with which an amplifier operates. For example, when an input signal at a level exceeding the first reference line 910 is input to the amplifier, the amplifier is saturated and; thus, does not normally amplify the input signal. In the graph of FIG. 9, a biosignal 920, which includes information on a desired bioimpedance to be measured, has a considerably large amplitude due to an interface impedance between an electrode and the object. The biosignal 920 includes all factors of an interface impedance in addition to the desired bioimpedance.

A compensation signal 930 used to compensate for the biosignal 920 has a phase opposite to a phase of the biosignal 920. The compensation signal 930 is used to reduce the factors of the interface impedance from the biosignal 920. The compensation signal 930 is generated based on the bioimpedance of the object or an additional impedance element, and a detailed description is found with reference to FIGS. 1A through 8.

The compensation signal 930 reduces an influence on the biosignal 920 due to the interface impedance by compensating for the biosignal 920. A combination signal 940 of the biosignal 920 and the compensation signal 930 have an amplitude smaller than an amplitude of the biosignal 920 and an amplitude of the compensation signal 930. Due to the combination, the amplitude of the biosignal 920 decreases by the amplitude of the compensation signal 930. The amplifier amplifies the combination signal 940. The biosignal 920 is amplified without saturating a measurement circuit because the compensation signal 930 decreases the amplitude of the biosignal 920. A second reference line 950 is a common DC signal component of the biosignal 920, the compensation signal 930, and the combination signal 940. The biosignal 920, the compensation signal 930, and the combination signal 940 have an identical frequency component.

Figure 10:
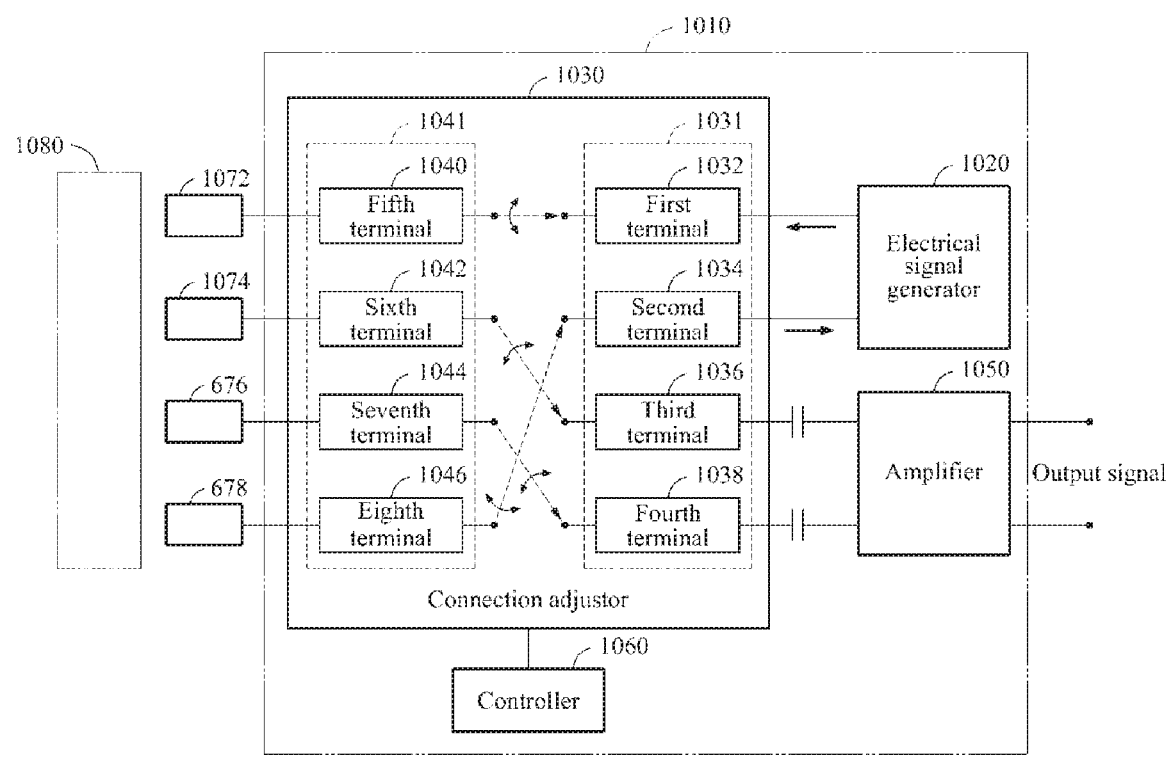
FIG. 10 is a diagram illustrating a still another example of an operation of a bioimpedance measuring apparatus, in accordance with an embodiment.

FIG. 10 is a diagram illustrating a still another example of an operation of a bioimpedance measuring apparatus 1010, in accordance with an embodiment. The bioimpedance measuring apparatus 1010 applies an electrical signal to an object 1080 through an electrode to measure a bioimpedance of the object 1080, and measures a biosignal generated in response to the electrical signal flowing into the object 1080 through another electrode. The biosignal includes information about the bioimpedance of the object 1080.

The bioimpedance of the object 1080 is estimated based on a level of the electrical signal applied to the object 1080 and a level of the measured biosignal. An interface impedance generated between the electrodes and the object 1080 varies depending on an electrode contact environment. The bioimpedance measuring apparatus 1010 changes the electrodes applying the electrical signal and the electrodes measuring the biosignal. Thus, changing the electrodes applying the electrical signal and the electrodes measuring the biosignal enable reduction in an influence of an interface impedance that may vary depending on each electrode and enables a precise measurement of the bioimpedance of the object 1080.

Referring to FIG. 10, the bioimpedance measuring apparatus 1010 includes an electrical signal generator 1020, a connection adjustor 1030, a controller 1060, and an amplifier 1050. The electrical signal generator 1020 generates an electrical signal to measure the bioimpedance. For example, the electrical signal is an AC signal or an AC voltage signal having a frequency component.

The connection adjustor 1030 adjusts connections between electrodes, for example, 1072, 1074, 1076, and 1078, that are electrically connected to the object 1080. The connection adjustor 1030 also adjusts connections between the electrical signal generator 1020 and the amplifier 1050. The controller 1060 generates a control signal to control the connection adjustor 1030. The connection adjustor 1030 determines, among the electrodes 1072, 1074, 1076, and 1078, the one or more electrodes to which the electrical signal generated by the electrical signal generator 1020 is transmitted based on the control signal. In an example, the connection adjustor 1030 includes switches, and connections between the switches adjusted based on the control signal output from the controller 1060.

The connection adjustor 1030 adjusts a connection of a first terminal group 1031 and a second terminal group 1041. The first terminal group 1031 includes a first terminal 1032 and a second terminal 1034 to which the electrical signal generated by the electrical signal generator 1020 is transmitted. The first terminal group 1031 also includes a third terminal 1036 and a fourth terminal 1038 that transmit the measured biosignal to the amplifier 1050. The second terminal group 1041 includes a fifth terminal 1040, a sixth terminal 1042, a seventh terminal 1044, and an eighth terminal 1046, which are connected to the electrodes 1072, 1074, 1076, and 1078, respectively. The connection adjustor 1030 adjusts the connection between the first terminal group 1031 including the first terminal 1032, the second terminal 1034, the third terminal 1036, and the fourth terminal 1038. The connection adjustor 1030 also adjusts the connection between the second terminal group 1041 including the fifth terminal 1040, the sixth terminal 1042, the seventh terminal 1044, and the eighth terminal 1046, which are electrically interfaced with the object 1080.

For example, at a first measuring stage, the first terminal 1032 are connected to the fifth terminal 1040, the second terminal 1034 to the eighth terminal 1046, the third terminal 1036 to the sixth terminal 1042, and the fourth terminal 1038 to the seventh terminal 1044. Thus, the biosignal transmitted from the sixth terminal 1042 and the seventh terminal 1044 are input to the amplifier 1050 via the third terminal 1036 and the fourth terminal 1038. At a second measuring stage, subsequent to the first measuring stage, the first terminal 1032 is connected to the sixth terminal 1042, the second terminal 1034 to the eighth terminal 1046, the third terminal 1036 to the fifth terminal 1040, and the fourth terminal 1038 to the seventh terminal 1044. Thus, the biosignal transmitted from the fifth terminal 1040 and the seventh terminal 1044 are input to the amplifier 1050 via the third terminal 1036 and the fourth terminal 1038. As illustrated in the foregoing, the bioimpedance measuring apparatus 1010 measures a biosignal including information on a bioimpedance a plural number of times by adjusting the connection between the first terminal group 1031 and the second terminal group 1041. Further, the bioimpedance measuring apparatus 1010 precisely measures the bioimpedance of the object 1080 based on the biosignal measured the plural number of times.

The amplifier 1050 amplifies the biosignal input through the third terminal 1036 and the fourth terminal 1038. In one illustrative example, the biosignal is input to the amplifier 1050 in a form of a differential signal. The bioimpedance measuring apparatus 1010 then outputs the amplified biosignal as an output signal.

Figure 11:
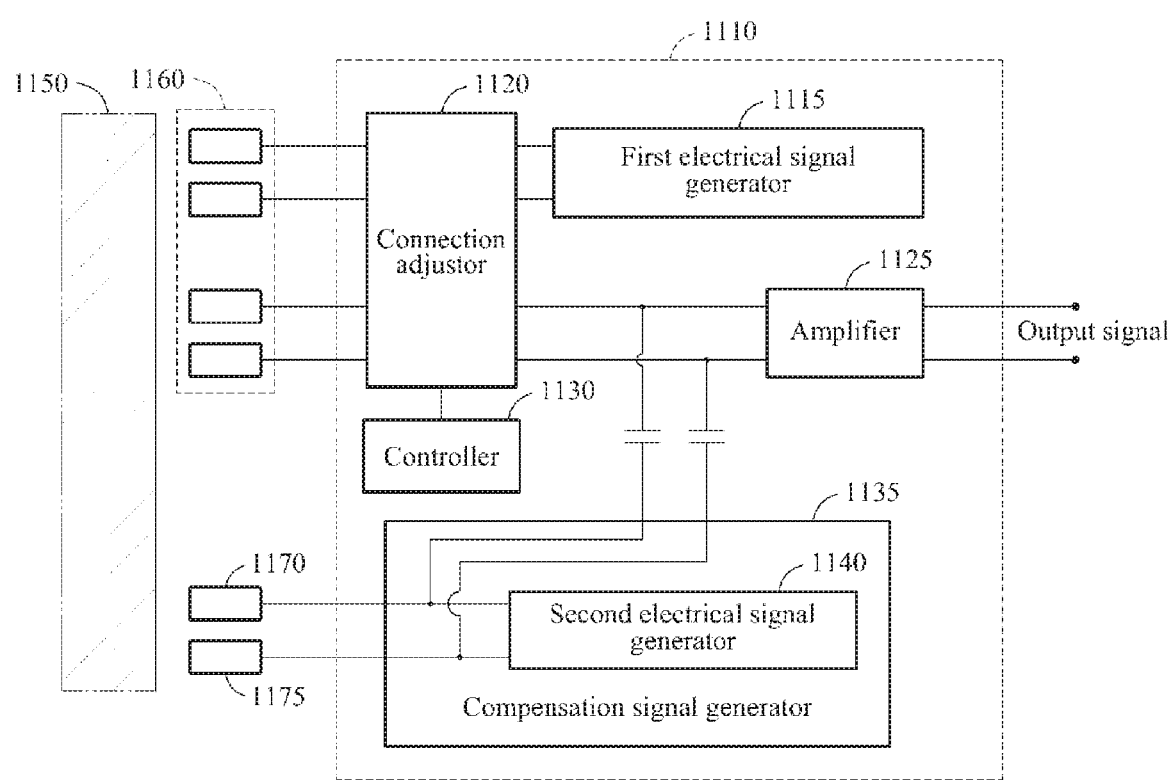
FIG. 11 is a diagram illustrating an example of an operation of a bioimpedance measuring apparatus including a connection adjustor, in accordance with an embodiment.

FIG. 11 is a diagram illustrating an example of an operation of a bioimpedance measuring apparatus 1110 including a connection adjustor 1120, in accordance with an embodiment. Referring to FIG. 11, the bioimpedance measuring apparatus 1110 includes a first electrical signal generator 1115, the connection adjustor 1120, a controller 1130, a compensation signal generator 1135, and an amplifier 1125. The compensation signal generator 1135 includes a second electrical signal generator 1140.

The first electrical signal generator 1115 generates a first electrical signal to measure a bioimpedance of an object 1150. The compensation signal generator 1135 generates a compensation signal to compensate for a biosignal generated by the first electrical signal flowing through the object 1150. The second electrical signal generator 1140 in the compensation signal generator 1135 generates a second electrical signal having a phase identical to or opposite to a phase of the first electrical signal. The second electrical signal is applied to the object 1150 through electrodes, for example, 1170 and 1175. The compensation signal is generated based on an interface impedance between the object 1150 and the electrodes 1170 and 1175. The amplifier 1125 amplifies the biosignal being compensated for by the compensation signal. The descriptions provided in FIGS. 1A through 2 pertaining to the first electrical signal generator 1115, the compensation signal generator 1135, the second electrical signal generator 1140, and the amplifier 1125 are incorporated herein.

The connection adjustor 1120 adjusts connections between electrodes 1160 electrically connected to the object 1150, the first electrical signal generator 1115, and the amplifier 1125. The controller 1130 outputs a control signal to control a connection between switches included in the connection adjustor 1120. The connection adjustor 1120 adjusts, based on the control signal, connections between terminals connected to the electrodes, terminals connected to the first electrical signal generator 1115, and terminals connected to the amplifier 1125. The bioimpedance measuring apparatus 1110 measures a predetermined number of times a biosignal that includes information about the bioimpedance of the object 1150. The compensation signal generator 1135 outputs the compensation signal to compensate the measured biosignal. The compensated biosignal is then input to the amplifier 1125. A combination signal of the biosignal and the compensation signal are amplified at the amplifier 1125, and the amplifier 1125 outputs the amplified combination signal as an output signal.

Figure 12:
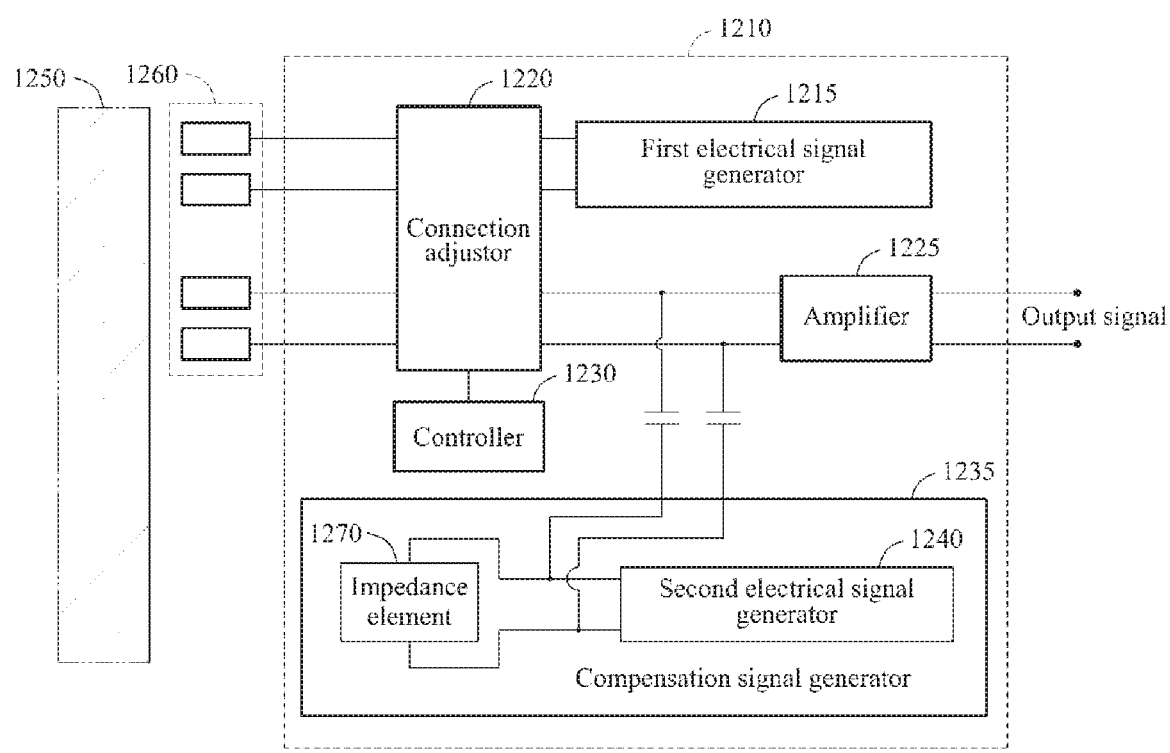
FIG. 12 is a diagram illustrating another example of an operation of a bioimpedance measuring apparatus including a connection adjustor, in accordance with an embodiment.

FIG. 12 is a diagram illustrating another example of an operation of a bioimpedance measuring apparatus 1210 including a connection adjustor 1220, in accordance with an embodiment. Referring to FIG. 12, the bioimpedance measuring apparatus 1210 includes a first electrical signal generator 1215, the connection adjustor 1220, a controller 1230, a compensation signal generator 1235, and an amplifier 1225. The compensation signal generator 1235 includes a second electrical signal generator 1240 and an impedance element 1270.

The first electrical signal generator 1215 generates a first electrical signal to measure a bioimpedance of an object 1250. The compensation signal generator 1235 generates a compensation signal to compensate for a biosignal generated by the first electrical signal flowing through the object 1250. The second electrical signal generator 1240 included in the compensation signal generator 1235 generates a second electrical signal having a phase identical to or opposite to a phase of the first electrical signal. The second electrical signal flows into the impedance element 1270, and the compensation signal is generated based on the second electrical signal and an impedance value of the impedance element 1270. The amplifier 1225 amplifies the biosignal being compensated for by the compensation signal. Descriptions of operations of the first electrical signal generator 1215, the compensation signal generator 1235, the second electrical signal generator 1240, and the amplifier 1225 may be found with reference to FIGS. 7A through 8.

Figure 13:
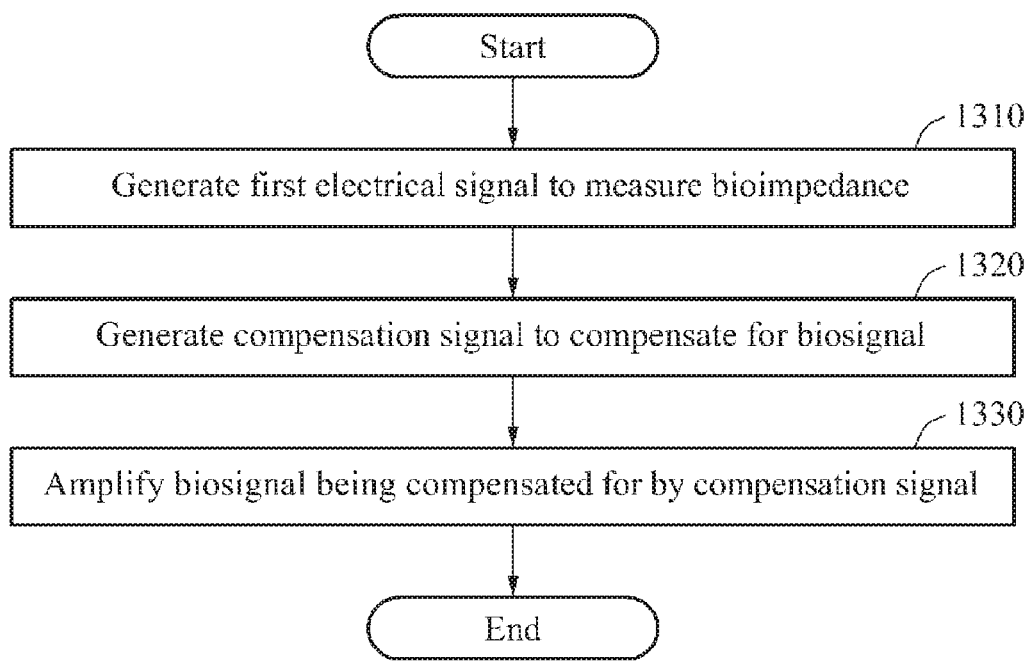
FIG. 13 is a flowchart illustrating an example of a bioimpedance measuring method, in accordance with an embodiment.

The connection adjustor 1220 adjusts connections among electrodes 1260 electrically connected to the object 1250, the first electrical signal generator 1215, and the amplifier 1225. The controller 1230 outputs a control signal to control a connection between switches included in the connection adjustor 1220. The connection adjustor 1220 adjusts, based on the control signal, connections between terminals connected correspondingly to the electrodes, terminals connected to the first electrical signal generator 1215, and terminals connected to the amplifier 1225. Thus, the bioimpedance measuring apparatus 1210 measures a predetermined number of times a biosignal including information on the bioimpedance of the object 1250. The compensation signal generator 1235 outputs the compensation signal to compensate the measured biosignal. The compensated biosignal is then input to the amplifier 1225. FIG. 13 is a flowchart illustrating an example of a bioimpedance measuring method, in accordance with an embodiment.

Referring to FIG. 13, in operation 1310, the bioimpedance measuring method generates a first electrical signal to measure a bioimpedance of an object. The first electrical signal may be an AC signal or an AC voltage signal having a frequency component. The first electrical signal is applied to the object through electrodes. A biosignal is then generated by the first electrical signal flowing through the object. The biosignal is generated based on the first electrical signal flowing in the object and the bioimpedance of the object. The biosignal is measured through other electrodes.

In operation 1320, the bioimpedance measuring method generates a compensation signal to compensate for the biosignal. The bioimpedance measuring method generates a second electrical signal having a phase identical or opposite to a phase of the first electrical signal. The second electrical signal is an AC signal or an AC voltage signal having a frequency component identical to the first electrical signal. As described with reference to FIGS. 1A through 8, a combination relationship between the biosignal and the compensation signal may vary based on the phase of the second electrical signal.

The compensation signal is generated based on the bioimpedance of the object or an impedance element. In an example, the compensation signal is generated in response to the second electrical signal flowing through an interface impedance between the object and the electrodes. In another example, the compensation signal is generated at both terminals of the impedance element in response to the second electrical signal flowing through the interface impedance.

The bioimpedance measuring method adjusts an amplitude of the second electrical signal that is output from a second electrical signal generator based on an amplitude of the compensation signal. When the amplitude of the compensation signal is determined to be higher than a predetermined threshold range, the bioimpedance measuring method decreases the amplitude of the compensation signal by decreasing the amplitude of the second electrical signal. Conversely, when the amplitude of the compensation signal is determined to be lower than the predetermined threshold range, the bioimpedance measuring method increases the amplitude of the compensation signal by increasing the amplitude of the second electrical signal.

The biosignal is combined with the compensation signal for compensation. Therefore, an amplitude of the biosignal decreases by the amplitude of the compensation signal. The biosignal and the compensation signal may have phases opposite to each other and; thus, the amplitude of the biosignal may decrease due to the combination.

In operation 1330, the bioimpedance measuring method amplifies the biosignal being compensated for by the compensation signal. The bioimpedance measuring apparatus amplifies the compensated biosignal based on a gain of an amplifier and outputs the amplified biosignal as an output signal. The output signal output from the bioimpedance measuring method is post-processed, for example, filtered, and converted to a digital signal using an ADC. The bioimpedance of the object is estimated by analyzing the digital signal. The estimated bioimpedance is provided to a user through a display device and the like.

The units, impedance elements, controllers, adjustors, generators, and amplifiers described herein may be implemented using hardware components. For example, the hardware components may include processors, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

It is to be understood that in the embodiment of the present invention, the operations in FIG. 13 are performed in the sequence and manner as shown although the order of some operations and the like may be changed without departing from the spirit and scope of the described configurations. In accordance with an illustrative example, a computer program embodied on a non-transitory computer-readable medium may also be provided, encoding instructions to perform at least the method described in FIG. 13.

Program instructions to perform a method described in FIG. 13, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein may be easily construed by programmers skilled in the art to which the embodiments pertain based on and using the flow diagrams and block diagrams of the figures and their corresponding descriptions as provided herein.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus to measure a bioimpedance, the apparatus comprising:
   a first electrical signal generator configured to generate a first electrical signal to measure a bioimpedance of an object;
   a compensation signal generator configured to generate a compensation signal to compensate a biosignal generated based on the first electrical signal and the bioimpedance; and
   an amplifier configured to amplify the compensated biosignal,
   wherein the compensation signal generator is configured to adjust an amplitude of a second electrical signal based on a comparison of an amplitude of the compensation signal and a predetermined threshold range, and the compensation signal generator is configured to generate the compensation signal in response to the second electrical signal flowing from electrodes into the object.

2. The apparatus of claim 1, wherein
   the compensation signal comprises a phase opposite to a phase of the biosignal, and
   an amplitude of the compensated biosignal is smaller than an amplitude of the biosignal before the compensation.

3. The apparatus of claim 1, wherein the compensation signal generator comprises a second electrical signal generator configured to generate the second electrical signal comprising a phase identical to or opposite to a phase of the first electrical signal.

4. The apparatus of claim 3, wherein
   the electrodes from which the second electrical signal flows into the object comprise two electrodes applying the second electrical signal into the object, and
   a distance between the two electrodes is shorter than a distance between two electrodes measuring the biosignal.

5. The apparatus of claim 3, wherein the compensation signal generator further comprises an impedance element configured to generate the compensation signal based on the second electrical signal.

6. The apparatus of claim 3, wherein the compensation signal generator generates the compensation signal in response to the second electrical signal flowing through the object to compensate a biosignal generated based on the first electrical signal flowing through the object and based on an interface impedance between the object and electrodes.

7. The apparatus of claim 1, further comprising:
   a connection adjustor configured to adjust connections between other electrodes electrically connected to the object, the first electrical signal generator, and the amplifier; and
   a controller configured to output a control signal to control a connection between switches included in the connection adjustor.

8. The apparatus of claim 7, wherein the connection adjustor adjusts, based on the control signal, connections among terminals connected to the other electrodes, terminals connected to the first electrical signal generator, and terminals connected to the amplifier.

9. The apparatus of claim 1, further comprising:
   a first capacitor between an electrode, at which the biosignal is measured, and a node, at which the biosignal and the compensation signal are combined; and
   a second capacitor between a node, at which the compensation signal is output, and the node, at which the biosignal and the compensation signal are combined.

10. The apparatus of claim 1, further comprising:
    electrodes configured to conduct the first electrical signal or the biosignal to the object, and
    wherein at least one of the electrodes interfaces with the object in electrical regions.

11. A method of measuring a bioimpedance, the method comprising:
generating a first electrical signal to measure a bioimpedance of an object;
generating a compensation signal to compensate for a biosignal generated based on the first electrical signal and the bioimpedance; and
amplifying the compensated biosignal,
wherein the generating comprises adjusting an amplitude of a second electrical signal based on a comparison of an amplitude of the compensation signal and a predetermined threshold range, and generating the compensation signal in response to the second electrical signal flowing from electrodes into the object.

12. The method of claim 11, wherein the compensated biosignal comprises an amplitude smaller than an amplitude of the biosignal prior to compensation.

13. The method of claim 11, wherein the outputting of the compensation signal comprises:
generating the second electrical signal comprising a phase identical or opposite to a phase of the first electrical signal; and
measuring a biosignal generated in response to the second electrical signal flowing into the object and thereby flowing in the object, and outputting the measured biosignal as the compensation signal.

14. The method of claim 13, wherein
the electrodes from which the second electrical signal flows into the object comprise two electrodes applying the second electrical signal to the object, and
a distance between the two electrodes is shorter than a distance between two electrodes measuring the biosignal.

15. The method of claim 11, wherein the outputting of the compensation signal comprises:
generating a second electrical signal comprising a phase identical or opposite to a phase of the first electrical signal; and
outputting, as the compensation signal, an electrical signal generated in response to the second electrical signal flowing through an impedance element, and
wherein the biosignal is combined with the compensation signal to decrease an amplitude of the biosignal.

* * * * *